(12) United States Patent
Hautaviita et al.

(10) Patent No.: US 12,370,313 B2
(45) Date of Patent: Jul. 29, 2025

(54) MEDICAMENT DELIVERY DEVICE WITH USAGE MONITORING

(71) Applicant: SHL MEDICAL AG, Zug (CH)

(72) Inventors: Nikolaj Hautaviita, Bro (SE); Rasmus Renstad, Stockholm (SE); Daniel Säll, Segeltorp (SE); Stefan Gylleby, Stockholm (SE); Per Lindstedt, Värmdö (SE)

(73) Assignee: SHL Medical AG, Zug (CH)

( * ) Notice: Subject to any disclaimer, the term of this patent is extended or adjusted under 35 U.S.C. 154(b) by 442 days.

(21) Appl. No.: 17/961,015

(22) Filed: Oct. 6, 2022

(65) Prior Publication Data

US 2023/0025726 A1    Jan. 26, 2023

Related U.S. Application Data

(60) Continuation of application No. 16/847,297, filed on Apr. 13, 2020, now Pat. No. 11,717,613, which is a
(Continued)

(30) Foreign Application Priority Data

Feb. 9, 2015  (SE) .................................. 1550144-8

(51) Int. Cl.
*A61M 5/315*   (2006.01)
*A61M 5/20*    (2006.01)

(52) U.S. Cl.
CPC ...... *A61M 5/31501* (2013.01); *A61J 2200/30* (2013.01); *A61J 2205/60* (2013.01);
(Continued)

(58) Field of Classification Search
CPC ................ A61M 5/31501; A61M 5/20; A61M 2005/2013; A61M 2005/2073;
(Continued)

(56) References Cited

U.S. PATENT DOCUMENTS 8,361,026 B2   1/2013   Edwards et al.
8,639,288 B1   1/2014   Friedman
(Continued)

FOREIGN PATENT DOCUMENTS

CN   101848742 A   9/2010
CN   102427840 A   4/2012
(Continued)

OTHER PUBLICATIONS

International Search Report and Written Opinion for Int. App. No. PCT/EP2016/051458, completed Mar. 30, 2016.

*Primary Examiner* — Nathan R Price
*Assistant Examiner* — John A Doubrava
(74) *Attorney, Agent, or Firm* — McDonnell Boehnen & Berghoff LLP (57) ABSTRACT

A medicament delivery device is presented having a housing that is arranged to accommodate a medicament container, a drive unit operably arranged to act on the medicament container upon activation, an activation mechanism operably arranged to be operated by a user, an activation preventing mechanism operably arranged to prevent the activation mechanism to be activated, an usage management module arranged to be operated by a user, which usage management module is designed as an attachable unit to the medicament delivery device. First keying elements are arranged on the device and on the usage management module designed to interact with each other when attaching said usage management module, such as to cause a deactivation of the activation preventing mechanism to allow operation of the activation mechanism. The usage management module can include a monitoring circuit arranged to monitor the use of the medicament delivery device.

20 Claims, 10 Drawing Sheets

Related U.S. Application Data division of application No. 15/544,083, filed as application No. PCT/EP2016/051458 on Jan. 25, 2016, now Pat. No. 10,668,220.

(52) U.S. Cl.
CPC ............... *A61M 2005/2013* (2013.01); *A61M 2005/2073* (2013.01); *A61M 2205/13* (2013.01); *A61M 2205/276* (2013.01); *A61M 2205/332* (2013.01); *A61M 2205/3375* (2013.01); *A61M 2205/52* (2013.01)

(58) Field of Classification Search
CPC ........ A61M 2205/13; A61M 2205/276; A61M 2205/332; A61M 2205/3375; A61M 2205/52; A61J 2200/30; A61J 2205/60
See application file for complete search history.

(56) References Cited

U.S. PATENT DOCUMENTS

| | | |
|---|---|---|
| 9,358,343 B2 | 6/2016 | Wieselblad |
| 9,592,351 B2 | 3/2017 | Bjork et al. |
| 9,662,448 B2 | 5/2017 | Holmqvist |
| 9,724,475 B2 | 8/2017 | Krulevitch |
| 9,937,297 B2 | 4/2018 | Bergens |
| 10,420,898 B2 | 9/2019 | Daniel |
| 2001/0028308 A1 | 10/2001 | De La Huerga |
| 2009/0240240 A1 | 9/2009 | Hines et al. |
| 2010/0211005 A1* | 8/2010 | Edwards .............. A61M 15/008 604/82 |
| 2010/0286612 A1 | 11/2010 | Cirillo et al. |
| 2011/0313395 A1* | 12/2011 | Krulevitch ........ A61M 5/31525 604/82 |
| 2012/0065588 A1 | 3/2012 | Cirillo et al. |
| 2013/0041327 A1* | 2/2013 | Daniel ................ A61M 5/3243 604/228 |
| 2014/0379874 A1 | 12/2014 | Starr et al. |
| 2015/0032059 A1* | 1/2015 | Allerdings ............. G16H 40/63 604/189 |
| 2015/0363097 A1 | 12/2015 | Draper et al. |

FOREIGN PATENT DOCUMENTS

| | | |
|---|---|---|
| CN | 103347557 A | 10/2013 |
| CN | 104220116 A | 12/2014 |
| JP | 2013-521832 A | 6/2013 |
| JP | 2013-538639 A | 10/2013 |
| WO | 2007/081947 A2 | 7/2007 |
| WO | 2007/107564 A1 | 9/2007 |
| WO | 2010/128493 A2 | 11/2010 |
| WO | 2012/067584 A2 | 5/2012 |
| WO | 2013/120777 A1 | 8/2013 |
| WO | 2014/118108 A1 | 8/2014 |
| WO | 2014/184293 A1 | 11/2014 |

* cited by examiner

MEDICAMENT DELIVERY DEVICE WITH USAGE MONITORING

CROSS REFERENCE TO RELATED APPLICATIONS

The present application is a continuation of U.S. patent application Ser. No. 16/847,297, filed Apr. 13, 2020, which is a divisional of U.S. patent application Ser. No. 15/544,083, filed Jul. 17, 2017, now U.S. Pat. No. 10,668,220, which is a U.S. National Phase Application pursuant to 35 U.S.C. § 371 of International Application No. PCT/EP2016/051458 filed Jan. 25, 2016, which claims priority to Swedish Patent Application No. 1550144-8 filed Feb. 9, 2015. The entire disclosure contents of these applications are herewith incorporated by reference into the present application.

TECHNICAL AREA

The present disclosure relates to medicament delivery devices and in particular medicament delivery devices provided with mechanisms related to specific approved users.

BACKGROUND

There is a constant development of medicament delivery devices that are intended and designed to be used and handled by users that are not qualified nursing staff or physicians, i.e. handled by the patients themselves. Because the patients themselves handle the treatment, based on a specific treatment scheme, the physicians treating the patient have no direct information that the treatment schemes are followed as prescribed.

In order to obtain more information regarding the treatment, a number of devices have been developed that are capable of monitoring the dose delivery operations and to store this information. Some devices are also capable of transmitting the information to external storage locations that are accessible to a trained healthcare staff. This enables access to relevant dose delivery information to e.g. a physician of a patient.

Document U.S. Pat. No. 8,361,026 discloses a medicament delivery device that is arranged with a number of intelligent functions that may monitor the operation of the device. Among the functions are monitoring of appliance and/or adherence of the patient and uploading of the information to a suitable storage means of a remote device, where the latter could be a remote communication network, a computer, a smart phone, personal digital assistant, etc. Information could also be downloaded to the medicament delivery device to be accessible to the user, such as if the drug of a medicament in the device has been recalled by the manufacturer of the drug, that the drug has expired or updated user information. In this regard, the device is arranged with a number of switches that are activated during different functional stages.

The device according to U.S. Pat. No. 8,361,026 is very complex and thus costly. It would be an advantage if monitoring functionality could be provided also to simpler medicament delivery devices such as those that are disposed of after use. Regarding monitoring of adherence, it would also be an advantage if the device could only function when the monitoring functionality was active.

SUMMARY

The aim of the present disclosure is to remedy the drawbacks of the state of the art medicament delivery devices in this area. This aim is obtained by a medicament delivery device having the features of the independent patent claims. Preferable embodiments are found in the dependent patent claims.

The medicament delivery device as described herein may comprise a housing, which housing is arranged to accommodate a medicament container. The medicament container may be arranged with a suitable medicament delivery member that is capable of delivering a dose to a user. The medicament delivery member may be an injection needle, a mouth or nose piece or a nebulizer for inhaling the drug, etc. in order to deliver a dose, a drive unit may be operably arranged to act on the medicament container upon activation.

Further an activation mechanism may be operably arranged to be operated by a user, as well as an activation preventing mechanism operably arranged to prevent said activation mechanism to be activated. Thereby the activation preventing mechanism will not permit the delivery of a dose until certain criteria are met.

A usage management module is preferably arranged to be operated by a user, wherein the usage management module may be designed as an attachable unit to the medicament delivery device. In that respect, first keying elements may be arranged on the medicament delivery device as well as on the usage management module. The keying elements are designed to interact with each other when attaching said usage management module such as to cause a deactivation of the activation preventing mechanism to allow operation of the activation mechanism. Thus, with the usage management module attached, the medicament delivery device may be used to deliver a dose of medicament to a user.

Further, the usage management module may preferably comprise a monitoring circuit arranged to monitor the use of the medicament delivery device. With this solution, an "add-on" monitoring circuit is provided that is capable of monitoring the operation of the medicament delivery device during use, combined with an unlocking of the medicament delivery device. Thus, the suggested solution will ensure that a dose delivery operation is monitored by the usage management module, since the medicament delivery device cannot be used without it. Further, the usage management module can be used for a large number of medicament delivery devices. In this respect, even low-tech, low-cost disposable medicament delivery devices can be provided with monitoring functionality.

According to one favourable solution, the monitoring circuit may be activated upon attachment of the usage management module with the medicament delivery device. In this way it is ensured on the one hand that the monitoring circuit is active when the device is to be used, and on the other hand, there is a reduced risk that the monitoring circuit is activated prematurely, which could lead to a drainage of power from a power source. In this respect, the activation of the monitoring circuit is preferably automatic, thus not requiring any user interaction, which otherwise may lead to that the circuit is not active if the user has forgotten to activate it.

According to one feasible solution, the monitoring circuit may be activated upon a change of usage status of said medicament delivery device. The change of usage status may be different operations depending on the type of medicament delivery device and the desired point of activation. For instance, the monitoring circuit may be activated when a safety cap is removed, when a dose of medicament is set, when the device is primed before injection, for example. One favourable change of usage status when the monitoring circuit could be activated is upon an end of dose delivery operation. This has the advantage that it is ascertained that a dose delivery occurrence has been performed and monitored, i.e. that the patient is complying with the adherence scheme. If the device is activated before the dose delivery operation, it might be that for instance the safety cap is removed but then the patient does not use the device. A change of status is then monitored but the patient has not complied with the treatment scheme.

The monitoring circuit may preferably be arranged with sensor elements capable of monitoring and registering current status and status changes of the medicament delivery device upon use of the medicament delivery device. Status changes may for example be when a medicament container has been emptied and the there is an end of dose situation. This status change is a good registering point in that components inside the medicament delivery device that are moving during dose delivery come to a stop, which may be readily monitored.

In order to handle the registered status changes, the monitoring circuit may comprise storage elements capable of storing registered data derived during the monitoring and registering. The stored data may then be used later for evaluation purposes of the usage of the medicament delivery device.

The usage management module may further comprise at least one communication circuit designed and arranged to communicate with external communication elements. In this way, the monitored and registered data may be communicated to appropriate devices adapted and arranged to handle and evaluate the registered data. On the other hand, the external communication elements may be elements arranged inside the medicament delivery device, which elements can detect status changes and transmit the detected changes to the usage management module.

The communication circuits may comprise a number of different communication technologies, either alone or in combination, comprising near range communication technology, wireless local area network communication technology, digital cellular network communication technology. In this respect the communication circuits are preferably operable to transmit registered data derived during the monitoring and registering to external storage sources.

In addition to transmitting registered data from the usage management module, the communication circuits may also be operable to receive data pertaining to the usage of the medicament delivery device. Thereby, the usage management module may then further comprise a communication circuit operable to communicate with a user of the medicament delivery device. In this manner, the user may receive information, such as adherence or compliance information, based on the monitored and registered data that the usage management module has transmitted earlier.

Further information that might be valuable when evaluating the usage of the medicament delivery device may be the location of the user when administering a dose of medicament. Therefore, the usage management module may further comprises a global positioning circuit, capable of obtaining information regarding the actual position of the activated medicament delivery device and wherein the communication circuits are designed to transmit position information to external sources.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which

DETAILED DESCRIPTION

In the following description, the wording medicament delivery device will be used. In this context, medicament delivery devices may include a number of devices capable of delivering certain doses of medicament to a user, such as e.g. injection devices with or without injection needles, inhalers of all kinds, such as powder, aerosol driven, gas, nebulizers having mouth or nasal pieces, dispensers for medicament in tablet form, eye dispensers, crème/gel dispensers, etc. The medicament delivery devices may be of either disposable type or re-usable type and may be provided with medicament containers suitably arranged for specific drugs in specific forms.

In the following description, the wording smart devices will be used. In this context, smart devices may include electronic devices that are provided with processors that are capable of running computer programs as well as storage space to store programs as well as data retrieved from different external sources. It is further to be understood that the smart devices are provided with communication systems that are capable of communicating with data networks in order to access different databases. It is to be understood that databases may be accessed via the internet, so called cloud services, and/or databases that are connected directly to and accessed via local area networks. It is further to be understood that the smart devices in this context comprise some sort of human-machine interface for two-way communication. The human-machine interface may comprise displays, keyboards, microphones, loudspeakers, I/O-ports for connection of peripherals. Further the smart devices may be provided with antennas for wireless communication with the networks. Also, the smart devices may be arranged with receiving and transmitting mechanisms capable of communicating with short range wireless communication technologies like e.g. RFID, NFC or Bluetooth. The smart devices are also arranged with programs capable of establishing and handling the communication with RFID tags, NFC tags or Bluetooth circuits.

Further, the term "distal part/end" refers to the part/end of the device, or the parts/ends of the members thereof, which under use of the device, is located the furthest away from a delivery site of a patient. Correspondingly, the term "proximal part/end" refers to the part/end of the device, or the parts/ends of the members thereof, which under use of the device is located closest to the delivery site of the patient.

Figure 1:
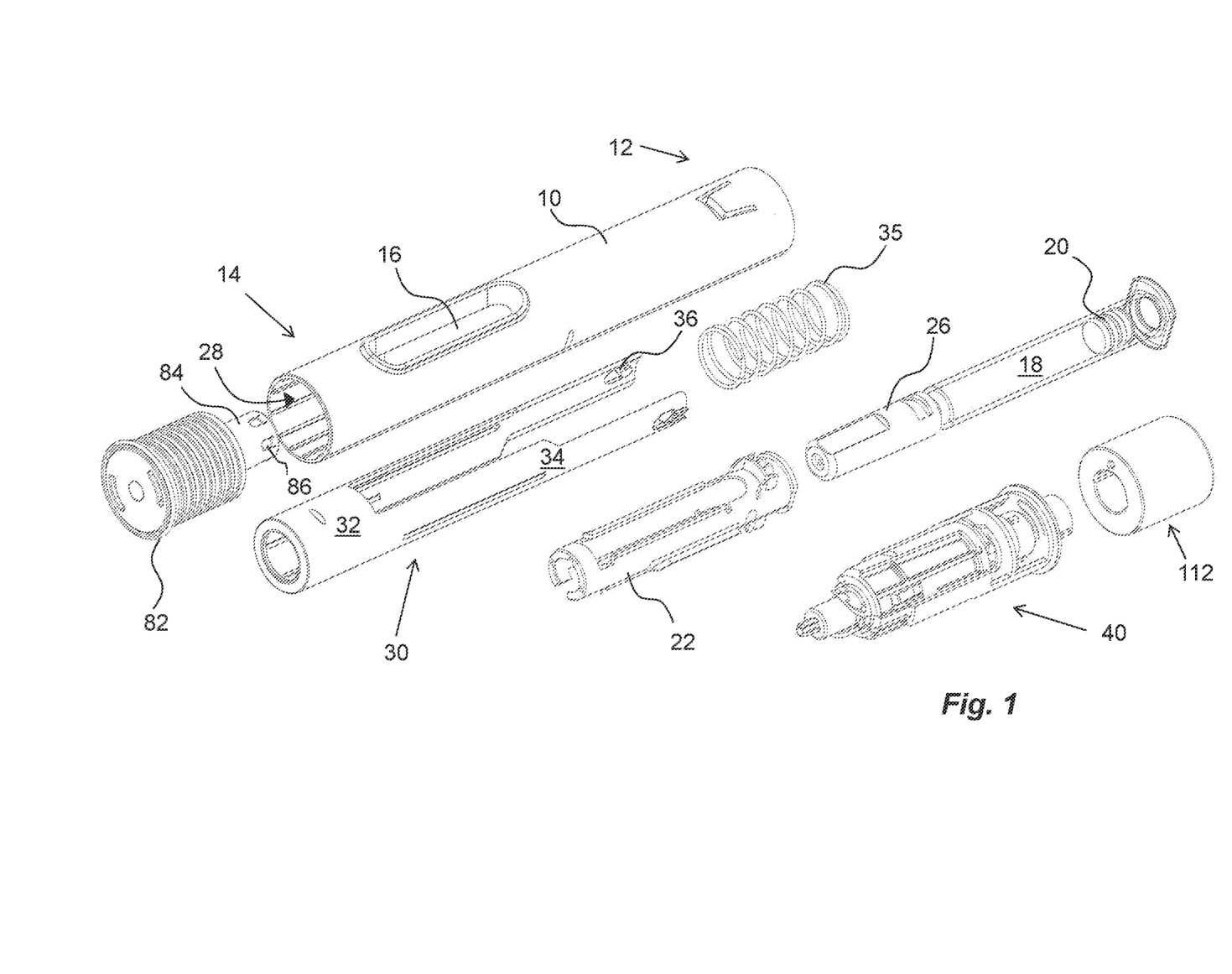
FIG. 1 is an exploded view of one embodiment of a medicament delivery device.
Figure 2:
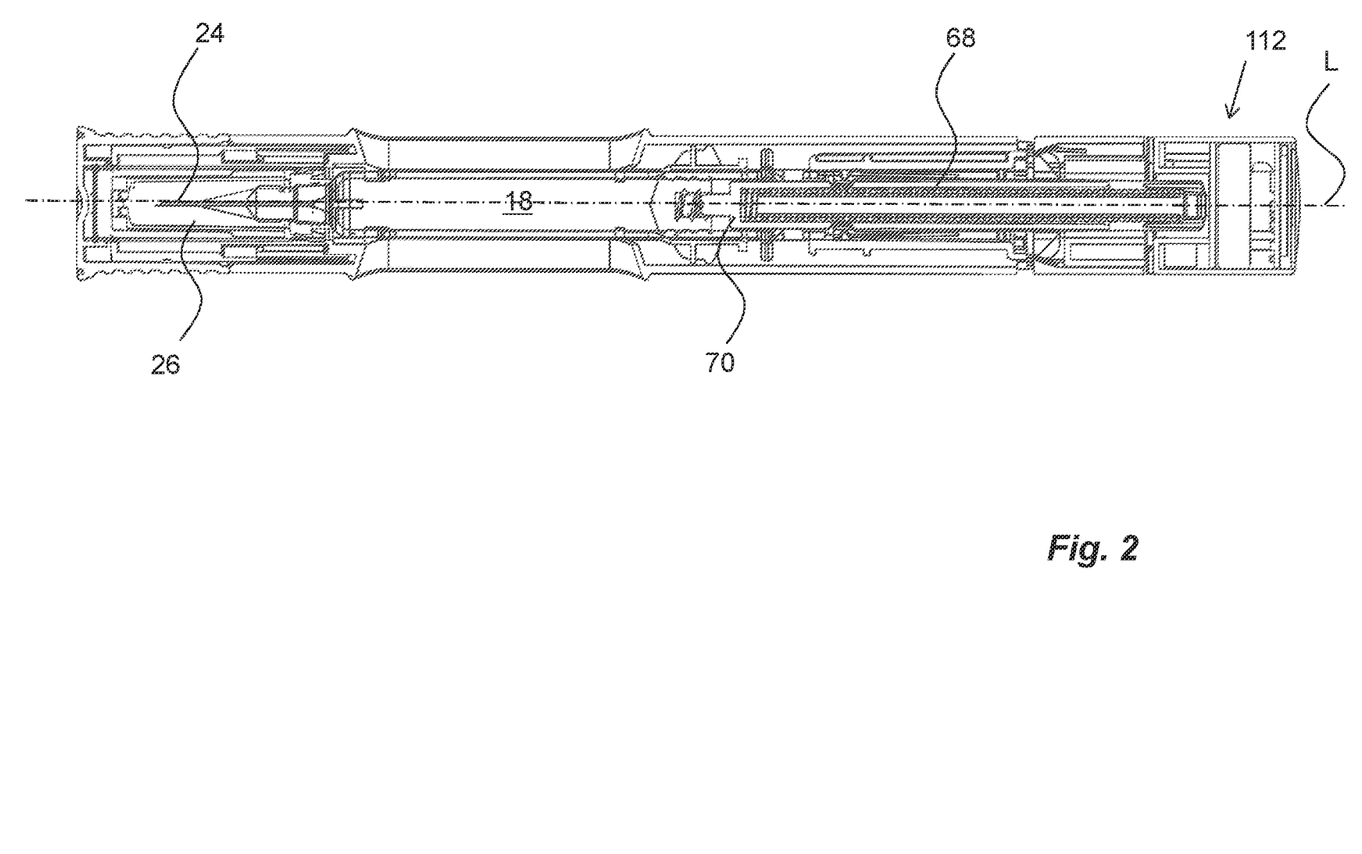
FIG. 2 is a cross-sectional side view of the device of FIG. 1, FIGS. 3, 4a, 4b, 5, 6, 7, 8, 9, 10 and 11 are detailed views of components comprised in the device of FIG. 1, FIGS. 12a and 12b comprise of exploded views of one feasible usage management module according to the disclosure.

The medicament delivery device shown in the drawings comprises a generally tubular elongated housing 10 having a distal end 12 and a proximal end 14, FIG. 1. The housing 10 is further arranged with windows or openings 16, through which a medicament container 18 can be viewed. The medicament container 18 is arranged with a movable stopper 20. The device further comprises a medicament container holder 22 having a generally tubular shape, FIG. 1. The medicament container holder 22 is arranged to accommodate the medicament container 18, where the medicament container 18 has a proximal end on which a medicament delivery member 24, FIG. 2, is arranged, either made integral or connectable to the medicament container 18. The medicament delivery member 24 is preferably protected before use by a medicament delivery member shield 26 that in the embodiment shown is a so called rigid needle shield or RNS. It is however to be understood that other types of medicament delivery member shields may be used in order to obtain the desired protection of the medicament delivery member 24.

The proximal end of the housing is arranged with a central passage 28, FIG. 1, through which a generally tubular medicament delivery member guard 30 extends. The medicament delivery member guard 30 is in this embodiment an activation mechanism of the medicament delivery device. It is arranged slidable in relation to the housing 10 such that the housing 10 with the medicament container 18 and the medicament delivery member 24 are moved in the proximal direction when the medicament delivery device is pressed against a dose delivery site, thereby exposing the medicament delivery member 24 such that a penetration is performed when the medicament delivery member is an injection needle.

The medicament delivery member shield comprises a proximal tubular 32 part and two distally directed arms 34 extending from the tubular part 32. A medicament delivery member guard spring 35 is arranged between a distally directed circumferential wall part of the medicament delivery member guard 30 and a proximally directed circumferential surface of the housing. The arms 34 are arranged slidable along the medicament container holder 22. At the distal end of the arms 34, inwardly directed protrusions 36 are arranged. The protrusions 36 are arranged to operably interact with a rotator 38, FIG. 3, of a drive unit 40, when the delivery member guard is moved in relation to the housing, wherein the rotator 38 is positioned distally of the medicament container 18.

Figure 3:
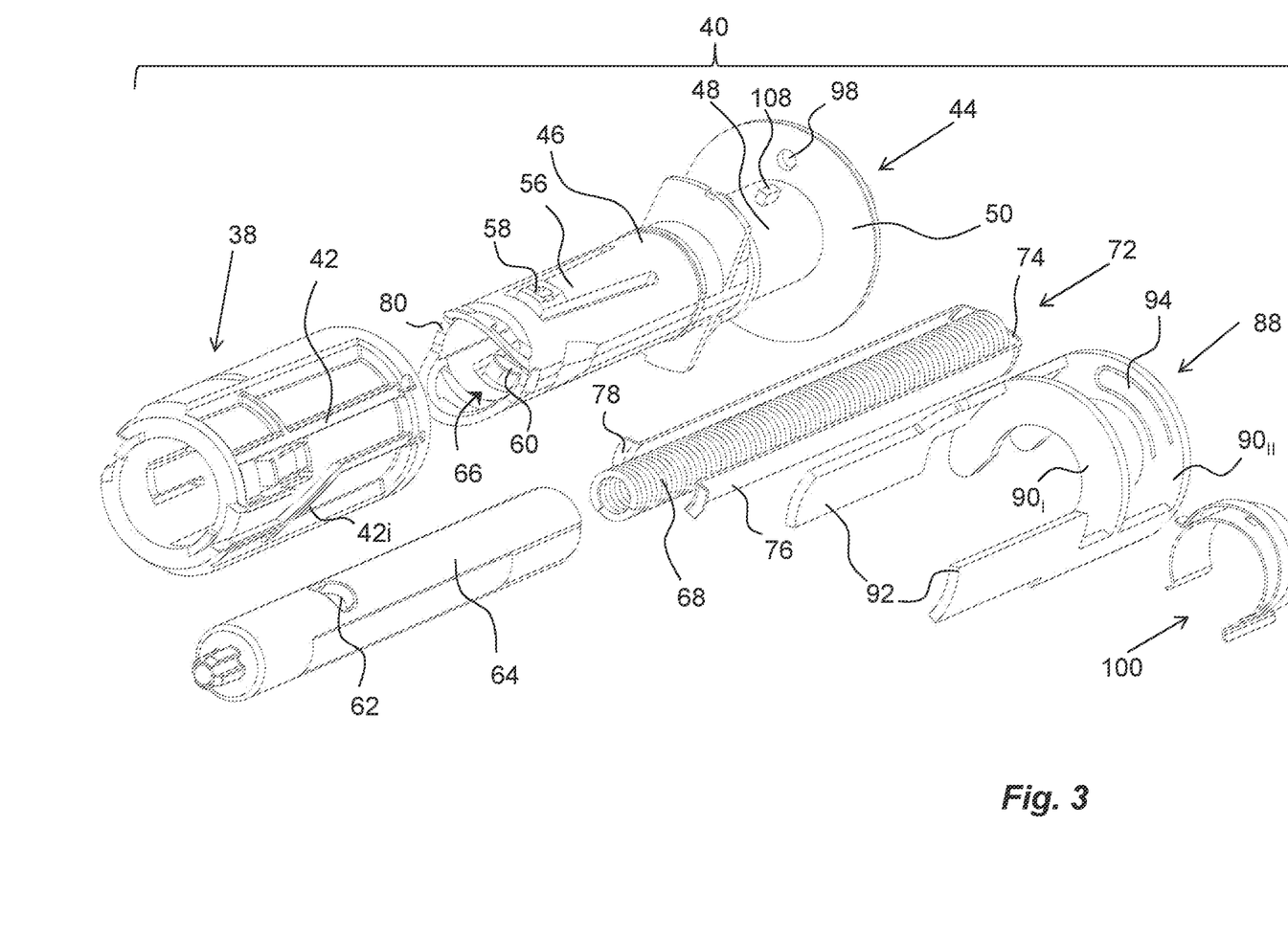

The rotator 38 has a generally tubular shape and is arranged with guide ridges 42 that are intended to cooperate with the protrusions 36 of the medicament delivery member guard 30 as will be described, wherein some sections $42_i$ of the guide ridges are inclined in relation to the longitudinal axis L of the device.

An actuator 44, FIG. 3, is further arranged operably to the rotator 38. It comprises a first proximal tubular section 46 having a diameter slightly smaller than the inner diameter of the rotator 38. It further comprises a generally tubular second section 48 arranged to fit into and to be attached to a distal part of the housing. The second section 48 is provided with a generally circular, radially extending, wall section 50.

The first section 46 is further arranged with proximally extending arms 56 that are arranged flexible in a generally radial direction. The free ends of the arms 56 have outwardly extending protrusions 58 that are to interact with inner surfaces of the rotator 38 as will be described. Further the free ends of the arms 56 are arranged with inwardly extending protrusions 60, which protrusions 60 are intended to interact with recesses 62 on a generally tubular plunger rod 64. The protrusions 60 extend into a central passage 66 of the actuator 44, in which passage 66 the plunger rod 64 fits.

The drive unit 40 further comprises a compression spring 68 placed inside a cavity of the hollow plunger rod 64, wherein the compression spring 68 is positioned with a proximal end thereof in contact with an end wall 70 of the plunger rod 64, FIG. 2. The distal end of the compression spring 68 is in contact with a generally U-shaped element, hereafter named activator 72, having a base 74 and two arms 76, FIG. 3. The arms 76 of the activator 72 are directed in the proximal direction along, and in contact with, the outer surface of the plunger rod 64, wherein the free ends of the arms 76 are arranged with generally radially outwardly directed ledges 78. These ledges 78 are arranged to be in contact with a proximally directed surface 80 surrounding the central passage 66 of the actuator 44.

The medicament delivery device is further arranged with a protective cap 82, FIG. 1, having a shape as to be releasibly attached to the proximal end of the housing. The protective cap 82 is further arranged with a medicament delivery member shield remover 84 that in the embodiment shown has a generally tubular shape with a diameter so as to extend into the medicament delivery member guard and surround the medicament delivery member shield 26. The medicament delivery member shield remover 84 is arranged with grip elements 86 that are inwardly inclined, proximally directed tongues that are capable of gripping into the surface of the medicament delivery member shield when the protective cap is pulled in the proximal direction in relation to the medicament delivery device.

As mentioned above, the medicament delivery member guard 30 is moved inside and relative the housing 10 when the medicament delivery device is pressed against a dose delivery site. This in turn causes the protrusions 36 of the medicament delivery member guard 30 to move along the guide ridges 42 of the rotator 38 such that the protrusions will come in contact with the inclined sections $42_i$, which will cause the rotator 38 to turn around the longitudinal axis L of the device.

The turning of the rotator 38 will cause the arms 56 of the actuator 44 to move out of contact with inner surfaces of the rotator 38. The arms 56 of the actuator 44 are now free to flex outwardly, whereby the inwardly directed protrusions 60 of the arms 56 are moved out of contact with the recesses 62 of the plunger rod 64.

The plunger rod 64 is now free to move in the proximal direction due to the force of the compression spring 68, wherein the proximal end of the plunger rod 64 acts on, and moves, the stopper 20 inside the medicament container 18 in the proximal direction such that a dose of medicament is expelled through the medicament delivery member 24.

Figure 5:
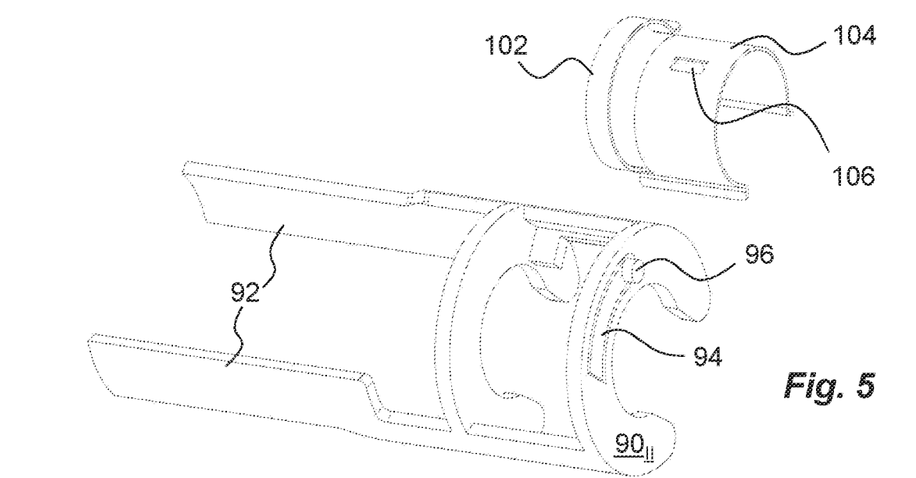

The medicament delivery device is further arranged with an activation preventing mechanism or a locking mechanism which is arranged to prevent use or activation of the medicament delivery device until the locking mechanism is activated. The activation of the locking mechanism may be performed in many ways that will be described below. According to one non-limiting example of a locking mechanism it comprises an activation preventing mechanism that in the embodiments shown is in the form of a blocking element 88, FIGS. 3 and 5. In the embodiment shown, the blocking element 88 is arranged with two semi-circular discs 90I and 90II, FIG. 3, oriented transversal to the longitudinal direction L and being adapted to fit around the second section 48 of the actuator 44.

Figure 4A:
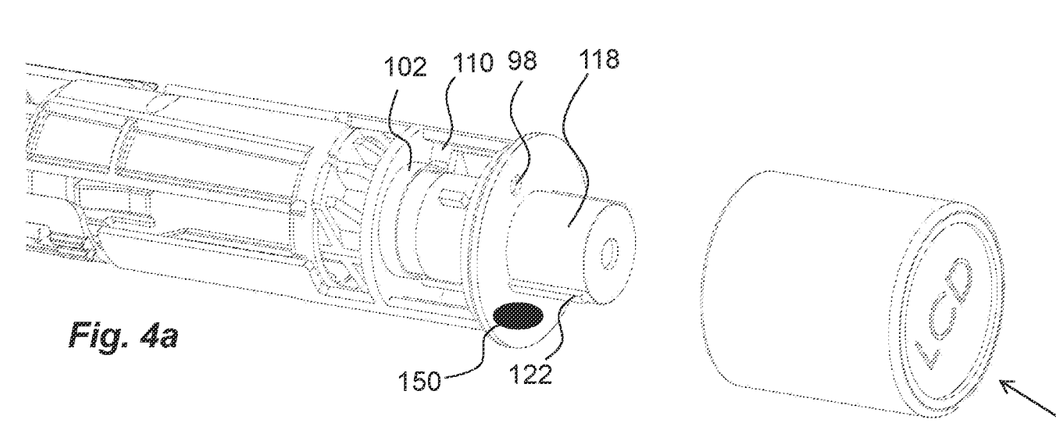
Figure 4B:
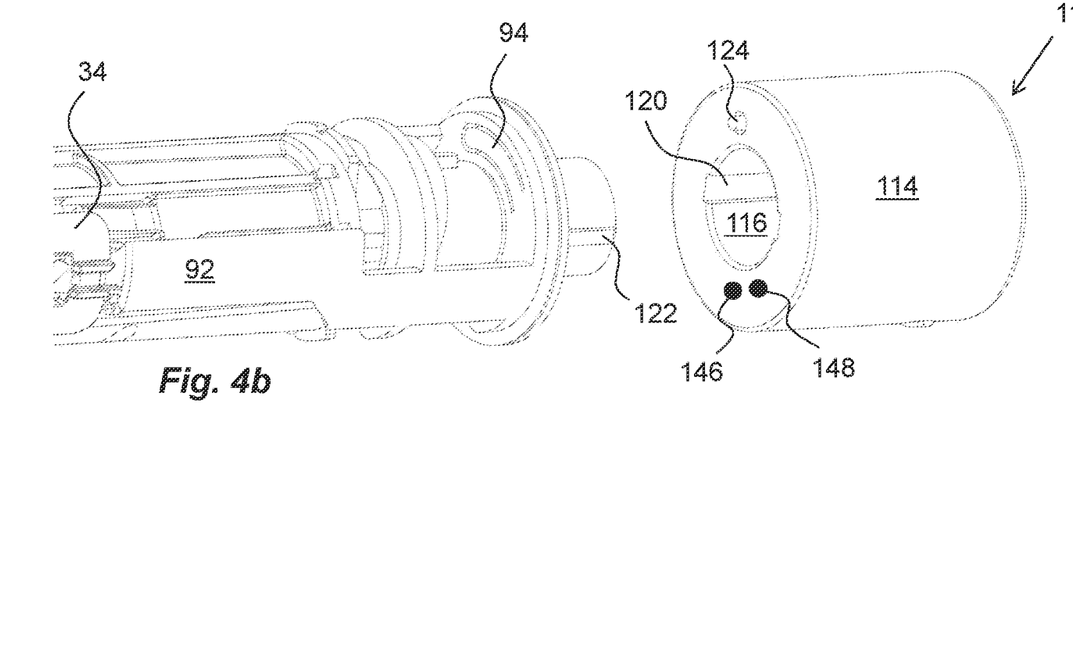

The blocking element 88 further comprises two proximally directed arms 92 positioned radially outside the rotator. As seen in FIG. 4b, wherein the device is in a non-activated state, the proximal ends of the arms 92 of the blocking element 88 are in contact with the distal ends of the arms 34 of the medicament delivery member guard 30. Thus, the medicament delivery member guard 30 is locked from being moved in relation to the housing 10 because the arms 34 of the medicament delivery member guard 30 are abutting the arms 92 of the blocking element 88, thereby preventing activation of the device.

Further, the blocking element 88 may be held in the locking position by a locking element. In the embodiment shown the most distally oriented disc 9011 is arranged with the locking element that in the embodiment shown comprises a flexible arm 94 formed through a generally U-shaped cut-out in the disc 9011, FIG. 5. The free end of the arm 94 is arranged with a distally directed protrusion 96, FIG. 5. The protrusion 92 is arranged and designed to fit into a passage 98, FIG. 3, in the wall section 50 of the actuator 44 when the locking element is in the locking position, whereby the position of the protrusion 96 in the passage 98 prevents any rotational movement of the blocking element 88.

Further, in the initial, locking position, a release element 100 is acting on the blocking element 88 with a force. In the embodiment shown, the release element 100 comprises a torsion spring 102, FIG. 5, shaped as an arch and attached to, or made integral with, a seat 104, which seat 104 is arranged to be attached to the second section of the activator. The seat 104 is arranged with a cut-out 106, in which a generally radially extending protrusion 108 on the second section 48 protrudes, FIG. 3, in order to lock the release element 100 rotationally. In the initial locked position, the torsion spring 102 is in a tensioned state with its free end resting against a ledge 110 of the blocking element 88 as seen in FIG. 4a.

In order to activate the medicament delivery device according to the disclosure, the blocking element 88 of the locking mechanism has to be affected such that the medicament delivery member guard 30 can be moved as described above. Further, the unlocking of the medicament delivery device should preferably activate a monitoring function such that current status and status changes of the device are monitored and registered. This is important from a device usage point of view in that there is a monitoring of whether or not the users comply to prescribed treatment schemes such as when a dose is taken, i.e. date and time. It should thus not be possible to use the device without the monitoring function being active, or at least it would be difficult to use the device alone.

In order to provide a monitoring function, which is connected to an unlocking operation of a medicament delivery device, a usage management module is comprised in the present disclosure. The usage management module 112 comprises a housing part 114 that is generally tubular, FIG. 4, having generally the same diameter as the housing 10 of the medicament delivery device, as seen in FIG. 2. The usage management module 112 is further arranged with keying elements that are arranged and designed to cooperate with the medicament delivery device when the usage management module is attached. In this regard, it is to be understood that the usage management module may have a number of designs depending on the desired appearance and for example the intended user. For instance, if the device is to be used by a child, the usage management module may be designed as e.g. the head of mickey mouse or spiderman, to give a positive feel when the device is to be used.

In the embodiment shown in FIG. 4, the keying elements comprise a central passage 116 with a proximally directed opening. The passage is arranged to fit onto a generally tubular distally directed post 118 of the medicament delivery device. Further, the central passage 116 is arranged with longitudinally extending grooves 120, two on opposite sides, whereby the post 118 is arranged with corresponding ridges 122 that fit into the groves 120, providing a rotational lock of the usage management module and a positioning aid. Further, the usage management module is arranged with a proximally extending pin 124, FIG. 4b. The pin 124 is positioned such that it will extend into the passage 98 when the usage management module 112 is attached to the distal end of the medicament delivery device.

Figure 6:
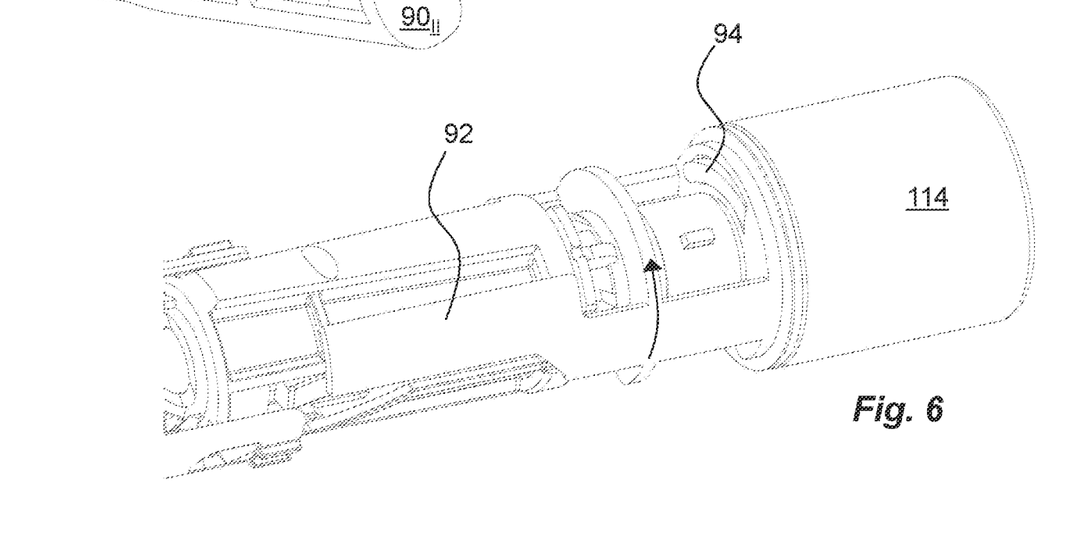

The extending of the pin 124 into the passage 98 will cause its proximal end to come in contact with the protrusion 96 of the arm 94 and will push the protrusion 96 out of the passage 98 against the bending force of the arm 94 as seen in FIG. 6. The torsion spring 102 of the release element 100 is now free to act on the blocking element 88 whereby its force on the ledge 110 will turn the blocking element 88 around the second section 48. The turning of the blocking element 88 will move the arms 92 of the blocking element 88 in a circumferential direction out of the locking position of the medicament delivery member guard, as seen in FIG. 6. The device may now be used as described above.

Figure 7:
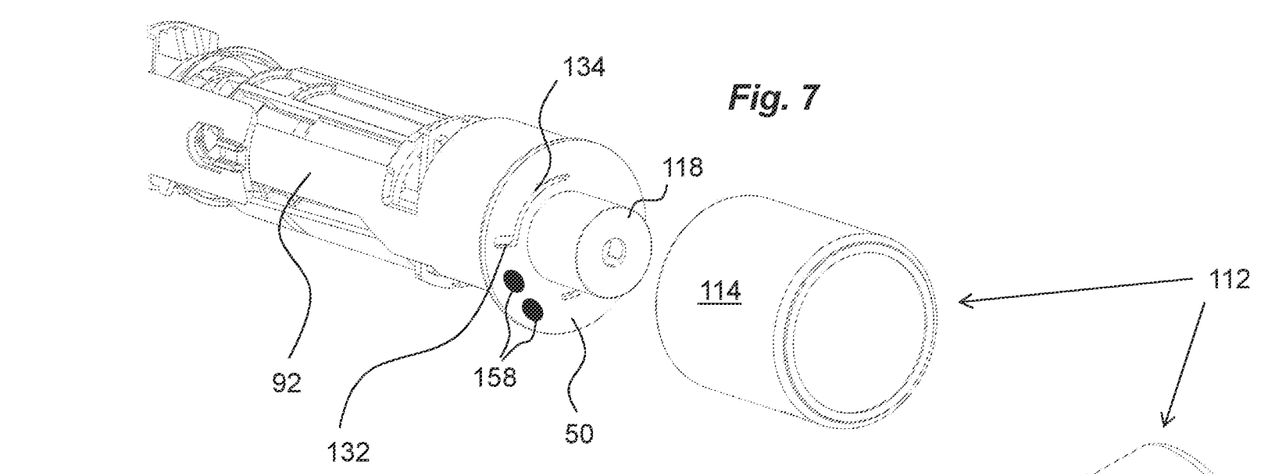
Figure 8:
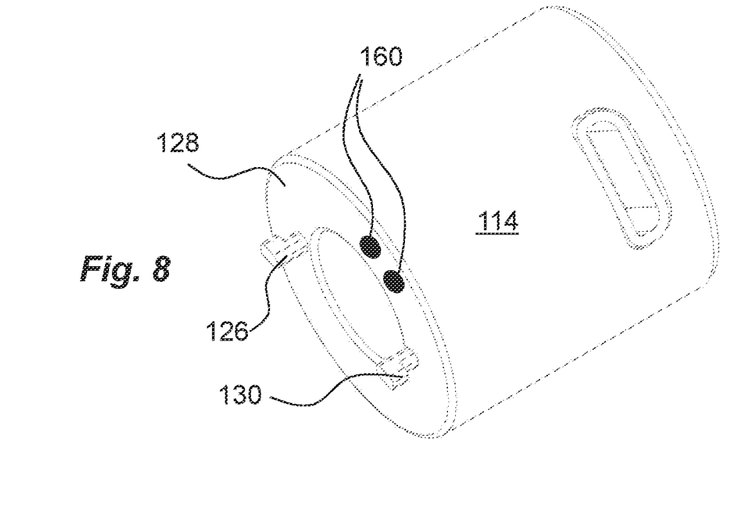
Figure 9:
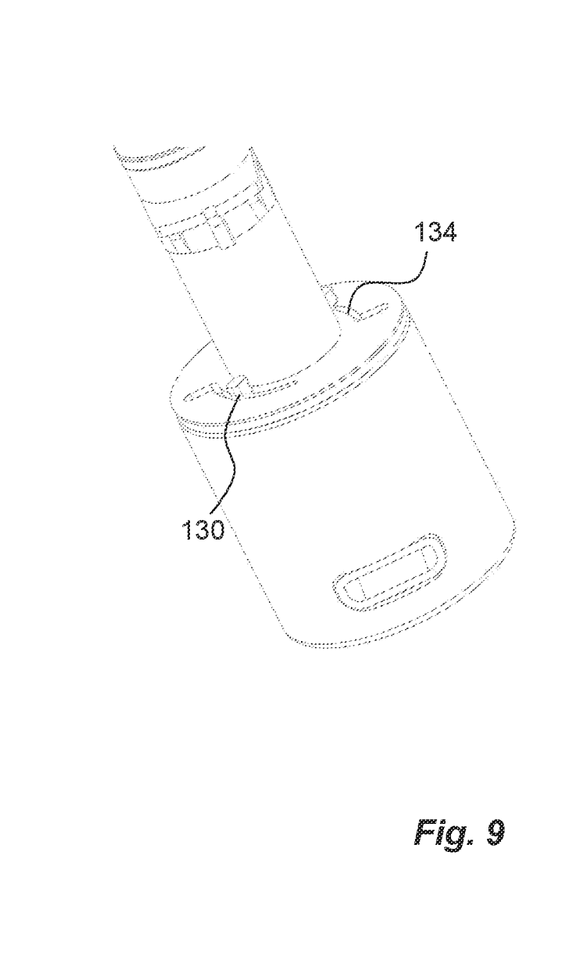

Another embodiment comprising keying elements is shown in FIGS. 7 and 8, where the usage management module 112 is arranged with keying protrusions 126, which keying protrusions are arranged on a proximally directed surface 128 of the usage management module 112. These keying protrusions 126 have radially outwardly directed ledges 130 such as to fit into radially extending grooves 132, FIG. 7, on the distal surface of the wall section 50. The radially extending grooves 132 are interconnected with generally arc-shaped grooves 134 on the wall 50 section, and when the usage management module 112 is turned around the post 118, the keying protrusions 126 will slide in the arc-shaped grooves 134 with the ledges 130 in contact with a proximally directed surface of the wall section 50, FIG. 9, thereby providing locking of the usage management module 112 in the longitudinal direction.

Figure 10:
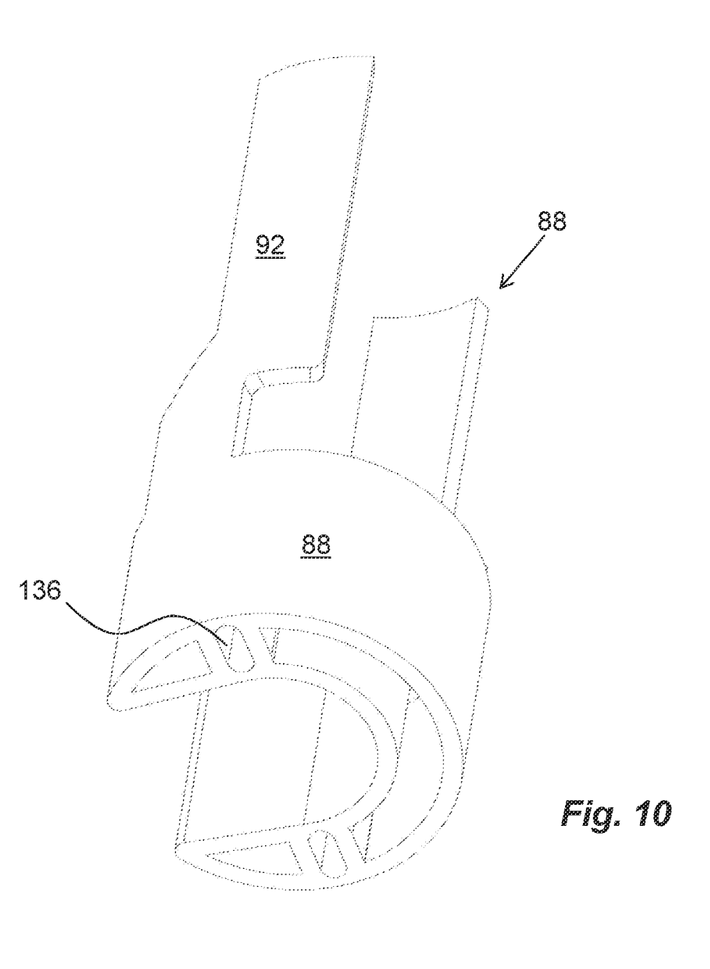
Figure 11:
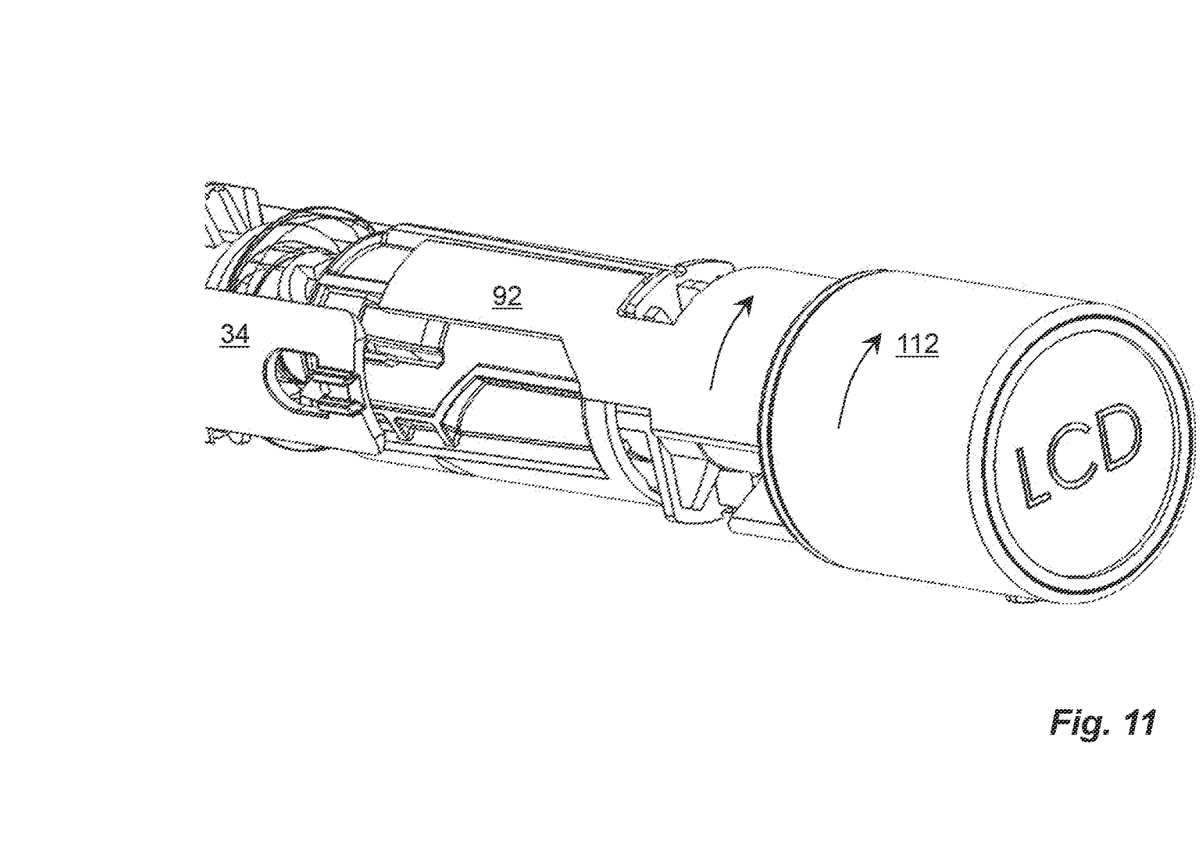

In this embodiment, the blocking element 88 is arranged with recesses 136 on its distally directed end surface, FIG. 10, the position of which corresponds to the keying protrusions 126 when they are positioned into the radially extending grooves 132 such that the keying protrusions 126 extend into the recesses 136 of the blocking element 88. When now the usage management module 112 is turned around the longitudinal axis L of the medicament delivery device, then the blocking element 88 also is turned. This will in turn move the arms 92 of the blocking element 88 out of contact with the arms 34 of the medicament delivery member guard 30, FIG. 11, whereby the medicament delivery member guard 30 is free to be moved as described above.

Figures 12A, 12B:
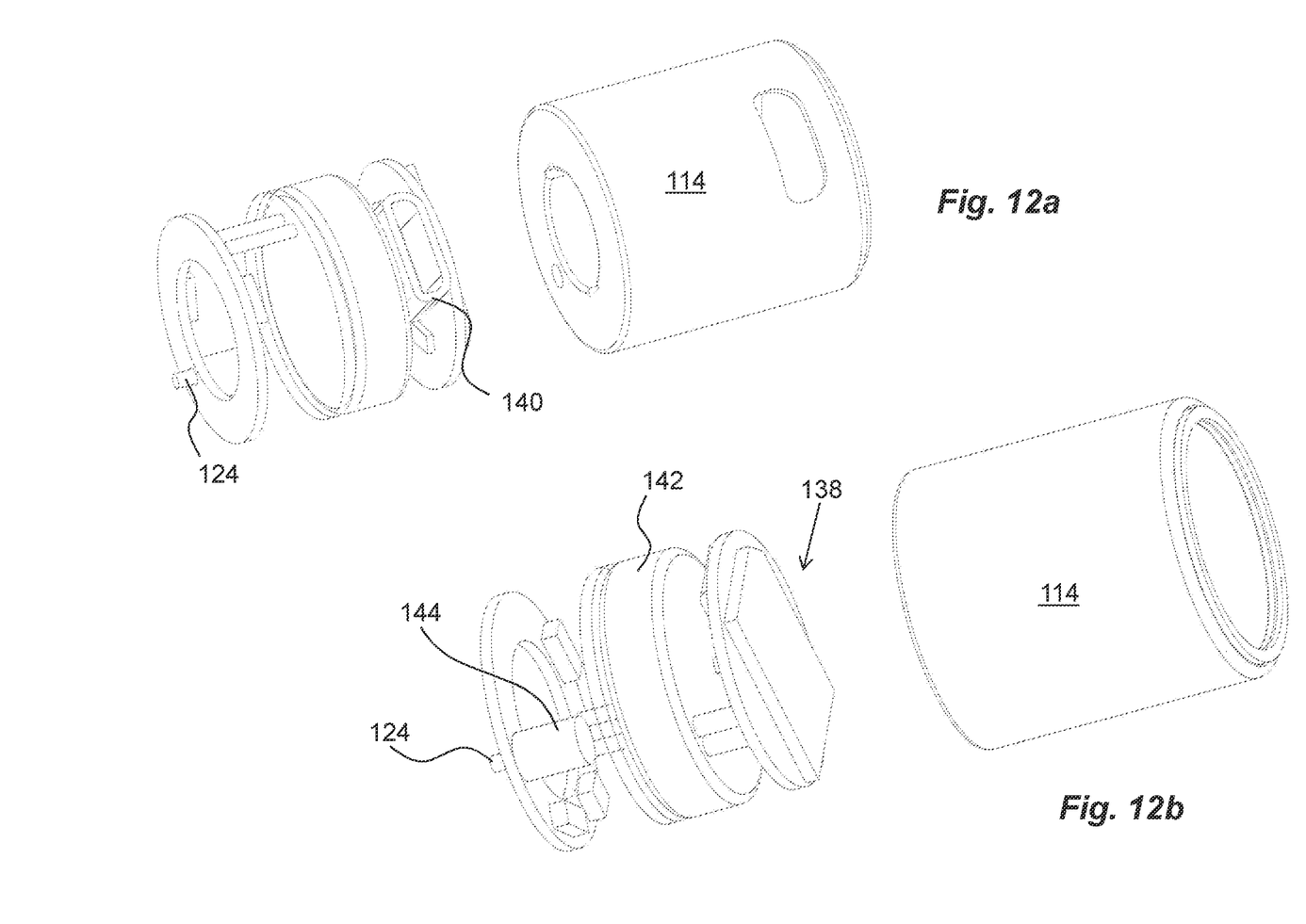

Also, as mentioned above, a monitoring function may preferably be activated by the attachment of the usage management module or at least when the medicament delivery device has been used, i.e. a status change has occurred of the device. In this regard the usage management module is arranged with electronic circuitry 138, FIG. 12b, which could comprise a number of features and components such as processors, I/O circuits, memory circuits, just to mention a few. The description below will give more examples applicable for the present disclosure. Further, appropriate connectors 140, FIG. 12*a*, may be arranged to the I/O circuits. The usage management module is preferably arranged with an appropriate power source such as a button cell 142. In order to activate the electronic circuitry of the usage management module and to "wake-up" the monitoring function, an appropriate switch is preferably arranged, operably connected to the circuitry.

The activation may be done at different stages upon handling of the medicament delivery device. As for the first embodiment, a switch may for example be arranged in connection with the pin of the usage management module such that when the pin 124 comes in contact with the protrusion 96 of the arm 94 and releases the blocking element 88, the pin 124 is also arranged to move a certain distance in the distal direction, thereby closing a circuit inside a switch unit 144, FIG. 12*b*, leading to an activation of the device upon attachment of the usage management module 112.

Another feasible solution regarding activation of the usage management module 112 is to provide the proximally directed surface with two electrical contact points 146, 148, FIG. 4*b*, where one is connected to the battery and the other to the circuitry 138. The distally directed surface of the wall section 50 could then be arranged with an area 150 having conductive material and positioned such that when the usage management module 112 is attached to the medicament delivery device, the contact points 146, 148 will both come in contact with the conductive area 150, providing a contact between the contact points, whereby the circuitry is powered up. This solution may also be used in connection with the second embodiment, where the turning of the usage management module 112 may close the electrical circuit in that the two electrical contact points 146, 148 and the conductive area 150 are positioned such that the contact points are moved into contact with the conductive area when the usage management module is turned into attachment positon, whereby a current can flow from one contact point to the other contact point via the conductive area, which current will activate the monitoring function of the usage management module.

The monitoring function may comprise a number of actions and operations that the medicament delivery device performs. One basic action that preferably is monitored is the delivery of a dose of medicament. According to one feasible solution the end of dose delivery is monitored and registered. In this respect, the switch that activates the usage management module may be arranged to obtain information or data from the medicament delivery device. For example the circuitry 138 of the usage management module 112 may be arranged with sensors that are capable of registering specific sounds or vibrations caused by components coming in contact with each other at the end of dose delivery, such as piezo-electric components that are capable of picking up sounds, whereby they will act as switches for the circuitry of the usage management module.

Figure 13A:
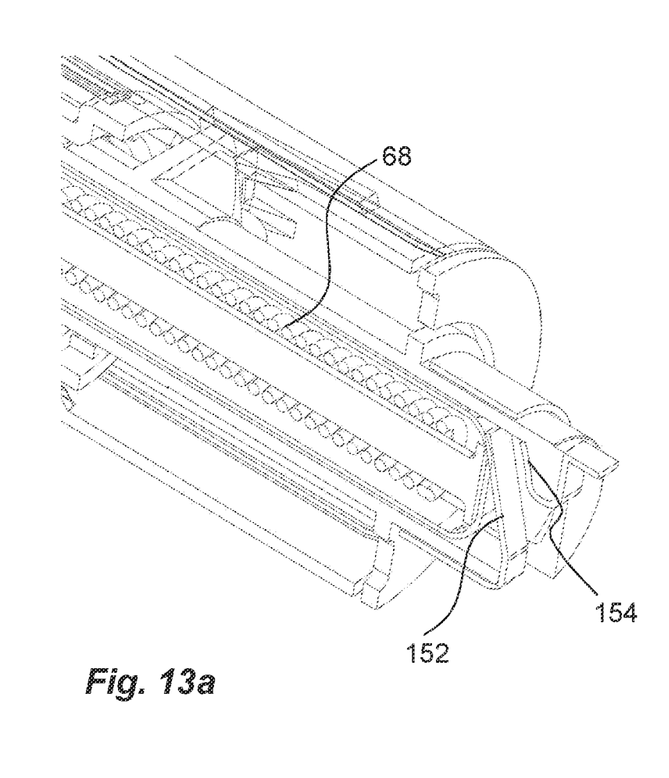
FIG. 13a is a perspective view of one embodiment where the end of a dose is registered and an electrically conductive material is in an open position.
Figure 13B:
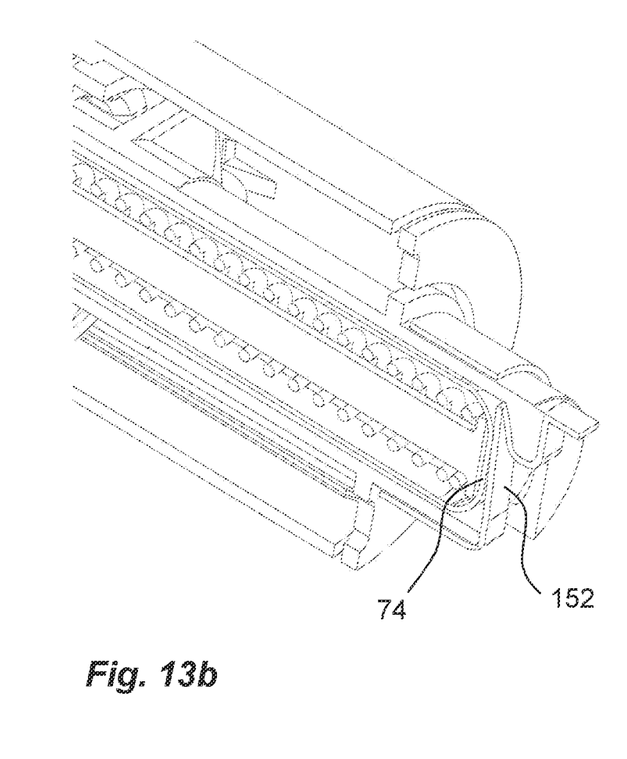
FIG. 13b shows the embodiment of FIG. 13a where the electrically conductive material is in a closed position.

Other designs of switches may incorporate electrical contacts positioned inside the medicament delivery device that are affected, opened/closed, when certain operations are performed in the medicament delivery device. For instance, when registering a dose delivery, a mechanical switch comprising electrical contacts may be arranged between two moving components, which switch is closed when the dose delivery sequence is ended. FIG. 13 shows one such solution where the end of a dose is registered. Near the end of a dose delivery when the plunger rod is moving in the proximal direction, the activator 72 is released from its attachment with the actuator 44. The activator 72 will then be moved in the distal direction by the force of the drive spring 68 acting on the base. The base will in turn act on a mechanical switch comprising a tongue 152 of electrically conductive material such that the tongue 152 will move from an open position as seen in FIG. 13*a*, to a closed position as seen in FIG. 13*b*, where the tongue 152 is moved in contact with a contact surface 154 and the switch is closed.

For this solution, appropriate conduits are provided inside the medicament delivery device, and an appropriate interface is provided between the proximal surface of the usage management module and the distal directed surface of the wall section, thereby providing an electrical contact between the medicament delivery device and the usage management module when attached. The interface could in a simple form be electrical contacts 158, FIG. 7, on the distally directed surface of the wall section 50 that connect to corresponding electrical contacts 160, FIG. 8, on the proximal surface of the usage management module 112 when attached.

In this respect, it is to be understood that other components may be arranged with switching or activation functionality in order to activate the usage management module but also for monitoring purposes. For instance, sensors may be arranged to identify that the protective cap has been removed earlier, and being put back again, which has adversely affected the sterility of the medicament delivery member. This information is transmitted to and stored in the usage management module. The information may then be retrieved from the usage management module by for example attaching an appropriate cable that has a connector corresponding to the connector of the usage management module. The other end of the cable may then be connected to a computer or a smart device for handling and processing of the information. It is also to be understood that certain switches and sensors may be arranged inside the usage management module in order to obtain switching or activation functionality.

In the above scenario, the usage management module may comprise a user communication circuit that is arranged and programmed to communicate with a user. The user communication circuit may comprise display elements that can communicate visually, e.g. by text stored in the electronics module that is displayed on a suitable display on the device. In addition to, or instead, the user communication circuit may comprise audio elements that can communicate audibly, e.g. by a recorded message stored in the electronics module that is played in an appropriate loudspeaker of the electronics module or of the device as such.

A further development of the activation function is to provide the usage management module with at least one communication circuit and to provide the medicament delivery device with data storage or data information providing elements. These communication technologies may comprise near range communication technology such as RFID, NFC or the like, as well as Bluetooth, Ant, Zigbee, just to mention a few. This type of wireless communication technology may then be used to activate the usage management module. For instance, the medicament delivery device may be arranged with a passive NFC-tag that could be comprised in a label attached to the medicament delivery device or embedded in the material of the medicament delivery device. The communication circuits of the usage management module are then capable of reading the NFC-tag when adjacent the medicament delivery device, whereby the usage management module is activated for monitoring. Also, the communication circuit may be used for monitoring the usage of the medicament delivery device such that information is transmitted from the medicament delivery device to the usage management module. For instance, a switch may be affected at the end of a dose operation, which may be detected by the NFC and transmitted to the usage management module.

In this regard, the NFC-technology may be used to register and derive additional information from the medicament delivery device. For instance, the medicament container may be provided with an NFC-tag that can be read by the NFC-circuit of the usage management module. The obtained information may then be stored in the usage management module and/or compared to pre-stored information. The information may comprise the type of drug that should be administered according to a treatment scheme, wherein the usage management module will authenticate the correct drug.

Regarding monitoring and registering of the status of the device as well as status changes, such as e.g. end of dose delivery sequence, the circuitry of the usage management module preferably is arranged with a timer function, by which it is possible to derive when a certain status change has occurred. There are many different techniques for providing this information, where on the one hand a program may be provided for the processor of the circuitry to handle date and time of occurrences and to store this information in the storage elements. This information may then be obtained by external sources when e.g. connecting the usage management module via its I/O-elements. On the other hand, the circuitry may instead be arranged with a counter that starts at the registered status change and when the usage management module is connected to an external source, the external source is capable of deriving the date and time of the occurrence by counting backwards the time the timer has counted from current time.

According to another possible feature, if the usage management module is provided with communication circuits, then monitoring data obtained by the usage management module may be transferred to external storage sources and/or external devices. If for instance NFC technology is used, then a mobile device being NFC-enabled may derive the monitored data from the usage management module. The mobile device may then either be capable of handling the data, such as e.g. calculating the time and date of an occurrence of the medicament delivery device, or may in turn transmit the monitored data to external databases via the communication technologies of the mobile device, such as cellular radio communication networks, e.g. GSM, 3G, 4G, etc. and/or wireless local area networks, which networks can provide access to the internet and thus to a large number of external data storage sources, data handling centres, etc.

Regarding communication technologies, it is of course possible to incorporate the above mentioned communication technologies in the usage management module as such. Then the usage management module may communicate directly with external data storage sources, data handling centres etc. via the communication networks. The monitoring data may preferably be accessible to a physician or the like skilled person that is responsible for the treatment of the user of the medicament delivery device and who might have put together a treatment scheme. This retrieved monitoring data may then be evaluated to derive information such as adherence, and the lack of which may lead to measures from the physician. These measures may be that information is transmitted back to the usage management module via the communication circuits, which information retrieved by the usage management module may be communicated to the user via the user communication circuit, and in particular if the user has deviated from the prescribed treatment scheme. The user may in that respect also be informed what measures that need to be taken in order to remedy the deviation. The usage management module may further be arranged with a circuit that is arranged to transmit a signal or a short data message at periodic intervals to an external data information handling centre that preferably is the same as for the monitoring data.

The signal is sent periodically, providing information that the usage management module is functioning. If such periodic signals are received but no monitoring data is received, this is a clear indication that the user does not use the device as prescribed, i.e. non-adherence. Without a periodic signal, if no monitoring data is received, there would be an uncertainty whether the usage management module is functioning or not, i.e. that the power source of the usage management module may be depleted for instance or that it is a sign of non-adherence.

The usage management module may be arranged with further registering capabilities that may be activated for instance when a dose is delivered, which is monitored and registered by the usage management module. The electronic circuits may be arranged with a positioning function whereby the geographical position of the user may be obtained and used for different purposes. In this respect, the positioning may be obtained by different functions. Either the electronics module is provided with a GPS-function, whereby the actual position of the user when the dose is delivered is recorded by GPS coordinates. Another possibility is to use the GSM-function for locating the position. The GPS-function and the GSM-function may further be combined with a WIFI location function for improved indoors location.

Regarding the activation of the usage management module, the circuitry could preferably be arranged with a suitable switch-off functionality, such as a timer function that will switch off the power to the circuitry after a certain time period for instance after completed medicament delivery operation. This will prolong the life of the power source in that it is not active when no action is taking place.

In the above examples of preventing activation or blocking of the medicament delivery device, a medicament delivery member guard is blocked until activation. It is however to be understood that other activation mechanisms and thus elements of the medicament delivery device may be blocked, depending on the actual design of the device. For instance, an activation button may be blocked, a drive unit, such as a piston rod may be blocked or activation components are positioned out of contact with each other until the usage management module is attached.

It is to be understood that the embodiments described above and shown in the drawings are to be regarded only as non-limiting examples of the disclosure and that it may be modified in many ways within the scope of the patent claims.

The invention claimed is:

1. A medicament delivery device comprising
a housing;
a medicament container positioned in the housing;
a drive unit comprising a plunger rod and an activator, where the plunger rod is biased in a proximal direction and the activator is biased in a distal direction and has a distal end portion; and
a usage management module positioned at a distal end of the housing and comprising:
a monitoring circuit that monitors the use of the medicament delivery device; and
a switch having an electrical contact projecting longitudinally in the proximal direction, wherein when the medicament delivery device is activated, the plunger rod moves proximally from a biased position to an end of dose position and the activator moves distally from a biased position to a switched position, and wherein when the activator reaches the switched position the distal end portion causes the electrical contact to move the switch from an open state to a closed state such that the usage management module is powered and records data relating to an end of dose state of the medicament delivery device.

2. The medicament delivery device according to claim 1, wherein the distal end portion of the activator has a contact surface that engages the electrical contact to cause the switch to move to the closed state.

3. The medicament delivery device according to claim 1, wherein the activator is biased in the distal direction by a drive spring.

4. The medicament delivery device according to claim 1, where the monitoring circuit and the switch are operatively connected to a battery, where the battery supplies power to the monitoring circuit when the switch is in the closed state.

5. The medicament delivery device according to claim 1, wherein said monitoring circuit is arranged with sensor elements capable of monitoring and registering current status and status changes of said medicament delivery device upon use of the medicament delivery device.

6. The medicament delivery device according to claim 1, wherein said monitoring circuit comprises storage elements capable of storing registered data derived during the monitoring and registering.

7. The medicament delivery device according to claim 1, wherein said usage management module comprises at least one communication circuit designed and arranged to communicate with external communication elements.

8. The medicament delivery device according to claim 3, where a proximal end of the drive spring engages the plunger to move the plunger rod proximally when the medicament delivery device is activated.

9. The medicament delivery device according to claim 7, wherein said communication circuits comprise near range communication technology.

10. The medicament delivery device according to claim 7, wherein said communication circuits comprise wireless local area network communication technology.

11. The medicament delivery device according to claim 7, wherein said communication circuits are operable to transmit registered data derived during the monitoring and registering to external storage sources.

12. The medicament delivery device according to claim 7, wherein the at least one communication circuit is operable to receive data pertaining to the usage of the medicament delivery device, wherein said usage management module further comprises a communication circuit operable to communicate with a user of the medicament delivery device.

13. The medicament delivery device according to claim 7, wherein said usage management module further comprises a global positioning circuit, capable of obtaining information regarding an actual position of the activated medicament delivery device and wherein the at least one communication circuit is designed to transmit position information to external sources.

14. The medicament delivery device according to claim 7, wherein the at least one communication circuit is arranged to communicate with communication elements arranged in the medicament delivery device.

15. The medicament delivery device according to claim 10, wherein said communication circuits comprise digital cellular network communication technology.

16. A medicament delivery device comprising
a housing comprising an open distal end;
a medicament container positioned in the housing and containing a medicament;
a drive unit comprising:
a hollow plunger rod;
a drive spring partially positioned in the plunger rod; and
an activator having a distal end portion, where the drive spring biases plunger rod in a proximal direction and the activator in a distal direction; and
a usage management module positioned in and closing the open distal end of the housing, where the usage management module comprises:
a monitoring circuit that monitors the use of the medicament delivery device;
a battery operatively connected to the monitoring circuit; and
a switch operatively connected to the battery and having an electrical contact projecting longitudinally in the proximal direction,
wherein during delivery of the medicament from the medicament container the drive spring moves the plunger rod proximally from a biased position to an end of dose position and moves the activator distally from a biased position to a switched position, and
wherein when the activator reaches the switched position the distal end portion causes the electrical contact to move such that the switch transitions an open state to a closed state such that the battery is electrically connected to the monitoring circuit and the usage management module records data relating to an end of dose state of the medicament delivery device.

17. The medicament delivery device according to claim 16, wherein a contact surface located on the activator moves proximally during the delivery of the medicament such that when the end of dose state is reached the contact surface will directly engage the electrical contact to cause the switch to move to the closed state.

18. The medicament delivery device according to claim 16, wherein the drive unit further comprises a rotator that is rotationally positioned within the housing and surrounding the plunger rod.

19. The medicament delivery device according to claim 18, wherein the drive unit further comprises a delivery member guard rotationally fixed relative to the housing and axially moveable relative to the rotator.

20. The medicament delivery device according to claim 19, wherein axially distal movement of the delivery member guard relative to a proximal end of the housing causes the drive spring to move the plunger rod proximally from the biased position.

* * * * *